(12) United States Patent
Park et al.

(10) Patent No.: US 11,242,397 B2
(45) Date of Patent: Feb. 8, 2022

(54) ANTI-CD40 ANTIBODY AND METHODS FOR BLOCKING CD40-CD40L SIGNALING

(71) Applicant: PB Immune Therapeutics Inc., Seoul (KR)

(72) Inventors: Chung Gyu Park, Seoul (KR); Jung Sik Kim, Anyang-si (KR)

(73) Assignee: PB Immune Therapeutics Inc., Seoul (KR)

( * ) Notice: Subject to any disclaimer, the term of this patent is extended or adjusted under 35 U.S.C. 154(b) by 186 days.

(21) Appl. No.: 16/618,736

(22) PCT Filed: Jun. 1, 2018

(86) PCT No.: PCT/KR2018/006327
§ 371 (c)(1),
(2) Date: Jun. 2, 2020

(87) PCT Pub. No.: WO2018/222019
PCT Pub. Date: Dec. 6, 2018

(65) Prior Publication Data
US 2020/0291123 A1   Sep. 17, 2020

(30) Foreign Application Priority Data
Jun. 1, 2017 (KR) ........................ 10-2017-0068350

(51) Int. Cl.
*A61K 39/395* (2006.01)
*C07K 16/28* (2006.01)
*A61P 37/06* (2006.01)
*A61K 45/06* (2006.01)
*A61K 39/00* (2006.01)

(52) U.S. Cl.
CPC .......... *C07K 16/2878* (2013.01); *A61P 37/06* (2018.01); *A61K 45/06* (2013.01); *A61K 2039/505* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2005/0136055 A1   6/2005   Gladue et al.
2014/0234334 A1   8/2014   Min et al.

FOREIGN PATENT DOCUMENTS

KR   20060111555   10/2006
WO      01/83755   11/2001
WO     2012/125569   9/2012

OTHER PUBLICATIONS

International Search Report and Written Opinion corresponding to International Application No. PCT/KR2018/006327 dated Sep. 7, 2018.
International Preliminary Report on Patentability corresponding to International Application No. PCT/KR2018/006327 dated Dec. 12, 2019.

*Primary Examiner* — Phillip Gambel
(74) *Attorney, Agent, or Firm* — Myers Bigel, P.A.

(57) ABSTRACT

The present invention relates to novel anti-CD40 antibodies and a use thereof and, more specifically, provided are a pharmaceutical composition for treating or preventing autoimmune diseases and a composition for inhibiting immune rejection during organ transplantation, both compositions containing, as an active ingredient, novel anti-CD40 antibodies that specifically bind to a novel epitope of CD40. Novel anti-CD40 antibodies of the present invention directly target CD40, but not CD40 ligands, and block the signaling of CD40-CD154 without stimulating platelets so as to exhibit excellent antagonistic effects, thereby being expected to be usable as a preparation effective in the treatment of autoimmune diseases and the inhibition of organ transplantation rejection.

15 Claims, 7 Drawing Sheets

Specification includes a Sequence Listing.

| | CYTOTOXICITY (%) | |
|---|---|---|
| | 4 HR | 20 HR |
| PBMC/RAJI/(-) | 1.29 | 2.24 |
| PBMC/RAJI/RM8G-1 [10.0]-3.3 µg/mL | 3.22 | 2.41 |
| PBMC/RAJI/RM8G-1 [1.0]-3.3 µg/mL | 3.06 | 2.25 |
| PBMC/RAJI/RM8G-1 [0.01]-3.3 µg/mL | 3.93 | 4.17 |
| PBMC/RAJI/RITUXAN [10.0] | 14.81 | 14.06 |
| PBMC/RAJI/RITUXAN [1.0] | 14.4 | 11.53 |
| PBMC/RAJI/RITUXAN [0.1] | 23.29 | 4.67 |

ANTI-CD40 ANTIBODY AND METHODS FOR BLOCKING CD40-CD40L SIGNALING

RELATED APPLICATIONS

This application is a 35 U.S.C. § 371 national phase application of PCT Application PCT/KR2018/006327 filed Jun. 1, 2018, which claims priority to Korean Application No. 10-2017-0068350 filed Jun. 1, 2017. The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 1547-2_ST25.txt, 3,917 bytes in size, generated on Jun. 7, 2021 and filed via EFS-Web, is provided in lieu of a paper copy. This Sequence Listing is hereby incorporated by reference into the specification for its disclosures.

FIELD OF THE INVENTION

The present disclosure relates to a novel anti-CD40 antibody and its use.

BACKGROUND OF THE INVENTION

A CD40 signal transduction pathway depends on combined regulations of many intracellular factors. Like other members of a TNF receptor family, CD40 binds with CD40L (either solid CD40L or soluble CD40L) and reacts with TRAF proteins (TNF receptor factor-binding proteins), such as TRAF2 and TRAF3, which mediate intracellular signals. TRAF converts the signal into a nucleus via map kinases such as NIK (NF-κB induced Kinase) and I-kappa B Kinase (IKK α/β), ultimately activates the transcription factor NF-κB (Young et al. (1998) Immunol. Today 19:502-06). Signaling via Ras and MEK/ERK pathways has also been demonstrated in a subset of B cells. Additional pathways included in the CD40 cell signaling include the PI3K/Akt pathway and the P38 MAPK pathway (Craxton et al. (1998) J. Immunol. 5: 439-447).

Signaling via CD40 has been shown to prevent cell death from apoptosis (Makus et al. (2002) J. Immunol. 14:973-982). Apoptosis signals are needed to induce planned cell death in a combined manner. Cell death signals may include intrinsic stimuli, such as cytoplasmic reticulum stress, or foreign stimuli, such as receptor binding of FasL or TNFα. Signaling pathways are complex and include the activation of caspases such as caspases 3 and 9, and the activation of poly (ADP ribose) polymerase (PARP). During cascade, members of anti-apoptotic signaling proteins such as members of Mcl-1 and BCLx, and IAP-family proteins, for example, X-binding inhibitors of apoptosis (XIAP) are downregulated (Budihardjo et al. (1999) Annu. Rev. Cell Dev. Biol. 15:269-90). Dendritic cell share CD40 cell signaling, for example, may block apoptosis signals converted by FasL (Bjorck et al. (1997) Int'l Immunol. 9:365-372).

Therefore, CD40 binding by CD40L and subsequent activation of CD40 signaling are essential steps for a normal immune response. This dysregulation of CD40 signaling may lead to autoimmune diseases (Ichikawa et al. (2002), J. Immunol. 169:2781-7 and Moore et al. (2002) J. Autoimmun. 19:139-45). Further, CD40/CD40L interactions also play an important role in inflammatory processes. For example, CD40 or CD40L are both overexpressed in human and experimental atherosclerotic lesions. CD40 stimulation induces expression of matrix-degrading enzymes and tissue factor expression in atheros-related cell types such as endothelial cells, smooth muscle cells, and macrophages. CD40 stimulation further induces the production of proinflammatory cytokines such as IL-1, IL-6, and IL-8, and adhesion molecules such as ICAM-1, E-selectin, and VCAM. Inhibition of the CD40/CD40L interaction prevents atherosclerosis in animal models.

CD40 is a 55 kDa cell-surface antigen that appears on the surface of normal and neonatal human B cells, dendritic cells, antigen presenting cells (APCs), endothelial cells, monocytes, CD8+T cells, and epithelial cells. CD40 antigen is also expressed in activated T cells, activated platelets, inflamed vascular smooth muscle cells, eosinophilic cells, synovial membrane of rheumatoid arthritis, fibroblasts of the skin, and other non-lymphoid cell types. Depending on the type of cell expressing CD40, ligation may induce intracellular adhesion, differentiation, activation, and proliferation. For example, binding of CD40 to CD40L as a cognate ligand thereof (also labeled CD154), stimulates B-cell proliferation and differentiation thereof into plasma cells, antibody production, isotype switching, and B-cell memory regeneration. During B-cell differentiation, CD40 is expressed on precursor B-cells but disappears when they differentiate into plasma cells.

CD40 ligands are identified on the cell surface of activated T cells (Fenslow et al. (1992) J. Immunol. 149:655; Lane et al. (1992) Eur. J Immunol. 22:2573; Noelle et al. (1992)) Proc. Natl. Acad. Sci. USA 89: 6550). However, the CD40 ligands are not normally expressed on stationary human T cells. CD40L is a type II transmembrane glycoprotein that has homology with TNF-α (Armitage et al. (1992) Nature 357:80 and Spriggs et al. (1992) J. Exp. Med. 176:1543). The extracellular domain of CD40L contains two arginine residues near a dura mater region and provides a potential proteolytic cleavage site that results in a soluble form of ligand (sCD40L). Overexpression of CD40L causes autoimmune diseases similar to systemic lupus erythematosus in rodent models (Higuchi et al. (2002) J. Immunol. 168:9-12). In contrast, the absence of functional CD40L on activated T cells leads to X-linked hyper-IgM syndrome (Allen et al. (1993) Science 259:990; and Korthauer et al. (1993) Nature 361:539).

In one example, type 1 diabetes is a metabolic disorder called insulin dependent diabetes mellitus and an is autoimmune disease. In a main mechanism, the destruction of beta cells (β cells) by T cells leads to insufficient insulin production, leading to failure of blood sugar control. According to the 2014 International Diabetes Federation statistics, 387 million people have diabetes. The number will be estimated to reach 592 million by 2035. In 2014, 49 million people died of complications from diabetes, and one patient dies from diabetes every 7 seconds.

There are several ways to treat the diabetes.

The first insulin-replacement therapy is an active insulin treatment that works in the short term but may not be a fundamental treatment. In the long run, insulin therapy does not prevent the risk of developing hypoglycemia, and thus does not prevents the occurrence of complications.

The second immunological approach as one of the most recent disease modifying therapies, involves immunomodulation or immunotolerance induction to prevent the progression of type 1 diabetes caused by the destruction of beta cells by attack of immune cells. For example, there is a method of inducing antigen specific T cell immune tolerance using a vaccine specific to beta cells. This immunological approach may prevent or delay the further destruction of beta cells. However, in general, when patients with the type 1 diabetes are diagnosed to have the type 1 diabetes, in most cases, only 10 to 20% of the beta cells remain. Thus, this approach using immunotolerance induction may be effective in a potential patient in which the diabetes may occur than in patients with the diagnosed type 1 diabetes. Antigen nonspecific immunomodulators are also effective only in early onset patients and thus a coverage thereof is very limited. The nonspecific immunomodulators affect the general immune system and cause side effects.

In the third regenerative approach, the number of beta cells may be expanded in order to meet the necessary metabolic requirements in pregnancy or obesity. This is known to be caused by differentiation of endocrine or non-endocrine cells of the pancreas or by proliferation of beta cells themselves. Among the drugs approved by the FDA, Dipeptidyl peptidase 4 (DPP4) inhibitors and Proton-pump inhibitors have been reported to increase GLP1 and gastrin in diabetic rats to induce beta cell proliferation and treat diabetes. However, the regenerative approaches have not been studied much and there are no clinical applications for regenerative approaches.

The fourth islet transplantation (Allogeneic/Xenogeneic islet transplantation) is the most effective and fundamental approach for treating type 1 diabetes by separating and transplanting islets containing beta cells from other persons (allogeneic) or swine (xenogeneic). For the islet transplantation, it is most important to develop immunosuppressive therapies that may effectively suppress the immune response of the recipient in response to the implanted islet. In early 2000, Edmonton protocols were developed using a combination of daclizumab (Zenapax), sirolimus (Rapamune), and tacrolimus (Prograf). Thus, allogeneic human pancreatic islet transplantation has become common. According to the Collaborative Islet Transplant Registry, 1,085 islet implants have been performed in 40 hospitals worldwide by 2013. Thus, insulin independence ratio exceeds 50% over five years. Since the islets are separated from 3 to 4 donors and then transplanted to a single recipient, the number of donors is far smaller than the number of the transplant recipients. Attempts have been made worldwide to isolate swine islet and transplant the same to the human (Xenogeneic porcine islet transplantation) to resolve the donor shortages.

Paradoxically, however, immunosuppressants currently used in allogeneic islet transplantation interfere with the engraftment of the implanted islet. Long-term use thereof not only causes various side effects to the recipients, but also leads to the death of islets, which is a major obstacle to the long-term survival of islets. Therefore, there is a need for the development of new immunosuppressive agents (or immunosuppressive antibodies) with fewer side effects and specific immune cell specificity.

At present, the ratio of insulin prescription dependence is very high. However, when the stability and efficacy of immunosuppressive agents are secured by the development of technology in the future, the scope of application thereof is expected to be gradually expanded.

Therefore, blocking the CD40-CD154 signaling in allogeneic and xenogeneic islet transplantation for the treatment of the type 1 diabetes is absolutely important in suppressing rejection and suppressing early diabetes development.

In other words, both anti-CD154 and anti-CD40 antibodies are known to induce the long-term survival of transplanted islets via inhibition of antibody production of B cell and activity inhibition mechanism of T cell in allogeneic and xenogeneic pancreatic islet transplantation model using primates. Blocking CD40-CD154 signaling of these immune cells is at a core of immunosuppressive therapy, thereby preventing the rejection of grafts by blocking the interaction of CD40/CD40L.

Therefore, it is necessary to develop a therapeutically and clinically relevant anti-CD40 antibody as a substance capable of effectively inhibiting CD40/CD40L interaction.

Blocking Cd40-CD40L signaling by the developed anti-CD40 antibody greatly suppresses immunity. Thus, autoimmune diseases treating agents, organ transplant immunosuppressants, chronic inflammatory diseases treating agents, and adjuvant agent via anti-drug antibody inhibition are expected to be developed.

DISCLOSURE

Technical Problem

Under these circumstances, the present inventors have made intensive studies to develop immunosuppressants to block the CD40-CD154 signaling for treatment of autoimmune diseases, suppression of immune rejection during organ transplantation, treatment of chronic inflammatory diseases, and adjuvant therapy via inhibition of anti-drug antibody formation. As a result, we have developed a novel anti-CD40 antibody (RM8G-1) that specifically binds to specific epitopes of human CD40. The novel anti-CD40 does not target the CD40 ligand but targets CD40 directly. The novel anti-CD40 blocks the CD40-CD154 signaling without stimulating platelets, thus indicating an excellent immunosuppressive effect. In this way, the present disclosure was completed.

Accordingly, it is an object of this invention to provide an anti-CD40 antibody epitope comprising CD40 amino acid residues of Glu58, Cys59, Leu60, Pro61, Cys62, Gly63, Glu64, Ser65, Glu66 and Phe67 of amino acid sequences of CD40.

It is another object of this invention to provide an anti-CD40 antibody or an antigen binding fragment thereof specifically binding to the epitope of the CD40.

It is still another object of this invention to provide a method of producing an anti-CD40 antibody or an antigen-binding fragment thereof specifically binding to the epitope, comprising injecting the epitope of the CD40 into non-human animals.

It is further object of this invention to provide a composition for blocking CD40-CD40L signaling, the composition comprising the anti-CD40 antibody or the antigen-binding fragment thereof.

It is still further object of this invention to provide a pharmaceutical composition for treatment or prevention of autoimmune diseases, the composition comprising the anti-CD40 antibody or the antigen-binding fragment thereof as an active ingredient.

It is still further object of this invention to provide a pharmaceutical composition for treatment or prevention of chronic inflammatory diseases, the composition comprising the anti-CD40 antibody or the antigen-binding fragment thereof as an active ingredient.

It is still further object of this invention to provide a composition for inhibiting immune rejection in organ transplantation, the composition comprising the anti-CD40 antibody or the antigen-binding fragment thereof.

It is still further object of this invention to provide a method for treating autoimmune diseases or chronic inflammatory diseases, the method comprising administering the pharmaceutical composition to a subject in need thereof.

Technical Solution

Unless defined otherwise, scientific and technical terms used in connection with the present disclosure have the meaning commonly understood by one of ordinary skill in the art. Further, unless otherwise indicated in the context, a singular term includes a single term, and plural terms. In general, the nomenclatures and techniques used in connection with cell and tissue culture, molecular biology, immunology, microbiology, genetics and protein and nucleic acid chemistry and hybridization disclosed herein are those well-known and commonly used in the art.

Hereinafter, the present disclosure will be described in more detail.

To achieve the purpose, according to one aspect of the present disclosure, the present disclosure provides an anti-CD40 antibody epitope comprising CD40 amino acid residues of Glu58, Cys59, Leu60, Pro61, Cys62, Gly63, Glu64, Ser65, Glu66 and Phe67 of amino acid sequences of CD40.

Further, according to another aspect of the present disclosure, the present disclosure provides an anti-CD40 antibody that specifically binds to the epitope of the CD40 and acts as a CD40 antagonist, or an antigen-binding fragment thereof.

It was first discovered by the present inventors that the anti-CD40 antibody or antigen-binding fragment thereof according to the present disclosure recognizes a novel epitope that is different from an epitope to which an antibody disclosed in the art binds.

In other words, the antibody in accordance with the present disclosure is different from conventional antibodies and is a superior antagonistic antibody that binds to the novel epitope and thus acts as an antagonist for CD40.

Further, unlike conventional antibodies, the present antibody recognizes linear antigens in addition to structural forms of the epitopes and binds thereto.

In accordance with the present disclosure, the anti-CD40 antibody or the antigen-binding fragment thereof may have, as the epitope, a CD40 region of 10 amino acids comprising 58# residue Glu, 59# residue Cys, 60# residue Leu, 61# residue Pro, 62# residue Cys, 63# residue Gly, 64# residue Glu, 65# residue Ser, 66# residue Glu, and 67# residue Phe, in CD40 as a region that the CD40 protein interacts with CD154. The anti-CD40 antibody or the antigen-binding fragment thereof may interfere with interaction with the CD154, and thus may effectively suppress the CD40-CD154 signaling. The CD40 is a protein encoded by the gene of PubMed Gene ID: 707749.

Further, the anti-CD40 antibody according to the present disclosure is characterized by: (i) high efficiency in blocking the CD40-CD154 binding, non-agonistic, non-depleting or minimal-depleting properties, novel epitope binding and high affinity. Thus, the anti-CD40 antibody according to the present disclosure meets all prerequisites for use as an anti-CD40 antibody for inhibiting immune-rejection in organ transplantation and treating autoimmune disease;

(ii) the anti-CD40 antibody according to the present disclosure may be applied to the primate/human cross-binding and thus it may be applied to non-clinical/pre-clinical testing, which is advantageous for the development of therapeutics, and may be specialized as an antibody that blocks (heterogeneous swine) CD40-(human) CD40L in xenograft/xenotransplantation. The anti-CD40 antibody according to the present disclosure meets all prerequisites for use as an anti-CD40 antibody for inhibiting immune-rejection in organ transplantation and treating autoimmune disease;

The anti-CD40 antibody according to the present disclosure may be used as an autoimmune disease treatment agent and an immunosuppressant for organ transplantation, which has excellent effects while meeting all the necessary requirements for developing the anti-CD40 antibody treatment agent.

As used herein, the term "antibody" refers to a protein that binds to another molecule (antigen) via a variable region of the light chain and heavy chain, and includes IgG, IgD, IgA and IgE types. Antibodies include polyclonal antibodies, monoclonal antibodies, and multispecific antibodies. Further, according to the present disclosure, the antibodies include monoclonal antibodies having various structures. This includes, for example, intact antibodies including two full-length heavy chains and two full-length light chains, as well as fragments, chimeric antibodies, human antibodies, humanized antibodies, or the like, including or free of an invariable region, or other genetically modified antibodies that are characterized by the present disclosure.

Further, in the present disclosure, "RM8G-1" used to refer to an antibody according to the present disclosure is no different from and thus is used interchangeably with "8G1" in the present disclosure.

As used herein, the term "antigen-binding fragment" refers to a portion of the intact antibody described above. The antigen-binding fragment is shorter by at least one sequence in length than the amino acid sequence of the intact antibody. The antigen-binding fragment includes at least a portion of an activity or function of an intact or parent antibody. For example, the antigen-binding fragment may include Fab (Fragment for antigen binding), Fab', F(ab')$_2$, Fv or SCA (Single Chain Antibody) (e.g. scFv or dsFv), bispecific scFv and diabody. However, the present disclosure is not limited thereto.

As used herein, the term "epitope" includes any protein determinant capable of specific binding to an immunoglobulin or T-cell receptor. The epitope determinant usually includes chemically an active surface grouping of molecules such as amino acids or sugar side chains and usually have specific tertiary structure characteristics as well as specific charge characteristics.

In the present disclosure, the epitope according to the present disclosure may bind to the anti-CD40 antibodies or antigen-binding fragments thereof according to the present disclosure, and may bind to a variety of antigen binding substances including peptides that complementarily bind to epitopes or chemical drugs. The variety of antigen binding substances may have similar or equivalent CD40-CD40L signaling blocking effects as in the anti-CD40 antibody according to the present disclosure. Various antigen binding materials including the chemical drugs or peptides may be included in the category according to the present disclosure.

According to a preferred embodiment according to the present disclosure, the CD40 is a primate CD40, wherein the primate includes humans, monkeys, chimpanzees, gorillas or orangutans, more preferably, human or monkey.

In one embodiment of the present disclosure, the anti-CD40 antibody or antigen-binding fragment thereof includes an immunoglobulin light chain variable region (VL) comprising an amino acid sequence set forth in SEQ ID NO: 1; and an immunoglobulin heavy chain variable region (VH) comprising an amino acid sequence set forth in SEQ ID NO: 2.

Further, the immunoglobulin light chain variable region (VL) includes the amino acid sequence of LCDR1 set forth in SEQ ID NO: 3, LCDR2 set forth in SEQ ID NO: 4 and LCDR3 set forth in SEQ ID NO: 5 as a complementarity-determining region (HCDR) sequence. The immunoglobulin heavy chain variable region (VH) includes the amino acid sequence of HCDR1 set forth in SEQ ID NO: 6, HCDR2 set forth in SEQ ID NO: 7 and HCDR3 set forth in SEQ ID NO: 8 as a complementarity-determining region (LCDR) sequence.

As used herein, the term "variable region" refers to an antigen binding region formed by portions of a heavy chain and a light chain. Each variable region includes four sequence-conserved backbones (FRs) and three complementarity-determining regions (CDRs) with severe sequence variations. CDR of the immunoglobulin heavy chain variable region (VH) is referred to as HCDR1 to HCDR3, while CDR of the immunoglobulin light chain variable region (VL) is referred to as LCDR1 to LCDR3.

As used herein, the term "complementarity-determining region" is a region that determines the specificity and binding ability of the antibody to the antigen. The sequence variation between the antibodies is found most frequently. In the CDR3 region, the most severe mutation occurs. The region has at least two amino acids and at most 26 amino acid residues. A portion other than the CDR in the VH and VL is framework residue. The framework of an antigen binding polypeptide according to the present disclosure may use a sequence found in human antibodies in nature or a sequence found in various antibodies as a common sequence.

The anti-CD40 antibody or antigen-binding fragments thereof according to the present disclosure may be provided in various forms as long as the anti-CD40 antibody or antigen-binding fragments thereof specifically recognize and bind to the epitope Glu58, Cys59, Leu60, Pro61, Cys62, Gly63, Glu64, Ser65, Glu66 and Phe67 of CD40 and thus blocks the interaction between CD40 and CD154.

The various forms including variations. The modification may be an anti-CD40 antibody or antigen-binding fragment thereof with reduced effector function, characterized by modification of the Fc portion of the antibody. The Fc-engineering may correspond to CDC by the Complement, or IgG4 or variants thereof lacking the ADCC effect by the cytotoxic cells.

That is, the modification corresponds to a variant in which the complement binding region of the IgG4 or the Fc or the Fc receptor binding region is modified and thus the CDC or ADCC function thereof is significantly reduced.

According to a preferred embodiment of the present disclosure, the antibody according to the present disclosure is selected from the group including monoclonal antibodies, chimeric antibodies, primate antibodies, humanized antibodies and human antibodies. More preferably, the antibody is a monoclonal antibody.

Further, the anti-CD40 antibody may be selected from the group including multimeric antibodies, heterodimeric antibodies, semidimeric antibodies, tetravalent antibodies, bispecific antibodies and single chain antibodies.

The antigen-binding fragment is selected from the group including Fab, F(ab)2, Fab', F(ab')$_2$, F(ab')$_3$, Fd, Fv and domain antibodies.

Those skilled in the art may construct an antibody including a component of an antibody including an invariable region using a variable region having sequence set forth in SEQ ID NOs: 3 to 8 as defined above.

Further, in the present disclosure, conservative substitutions may occur at amino acids in the SEQ ID NOs: 1 to 8. In the present disclosure, the substitutions may occur in the number of amino acids smaller than 10, smaller than 9, smaller than 8, smaller than 7, smaller than 6, smaller than 5, smaller than 4, smaller than 3, smaller than 2 or of 1.

As used herein, the term "conservative substitution" is a term commonly used in the art that refers to a substitution of one amino acid with another amino acid of similar feature. The similar features include, for example, size, hydrophobicity, or charge. Amino acids are usually classified as amino acids with positively charged side chains, negatively charged side chains, uncharged side chains or hydrophobic side chains, depending on the electrical characteristics of the side chains. For example, the conservative substitutions include substitutions of leucine (Leu) with isoleucine (ile), of arginine (Arg) with lysine (Lys), of phenylalanine (Phe) with tryptophan (Trp), of aspartic acid (Asp) with glutamic acid (Glu) or of serine (Ser) with threonine (Thr), or vice versa. In general, the conservative substitutions of CDR sequences do not have an essential effect on the function of the CDR.

Methods of the substitution of the sequences are known in the art, and are disclosed, for example, in Sambrook, Molecular Cloning [0053] A Laboratory Manual (Fourth Edition), Cold Spring Harbor Laboratory (2012) N.Y.

The antibodies according to the present disclosure include antigen-binding fragments, variants or derivatives thereof, and may include polyclonal, monoclonal, multispecific, human, humanized, primate, or chimeric, single-chain antibody, epitope binding fragments, such as fragments including Fab, Fab', F(ab')$_2$, F(ab)$_2$, Fd, Fvs, single-chain Fvs (scFV), disulfide linked Fvs (sdFv), VL or VH region. However, the present disclosure is not limited thereto. The antibody according to the present disclosure may be of any type, for example, IgG, IgE, IgM, IgD, IgA or IgY. Further, the antibody may be any class such as IgG1, IgG2, IgG3, IgG4, IgA1 or IgA2, or may be a subclass thereof.

The anti-CD40 antibody or antigen-binding fragment thereof according to the present disclosure may be a chimeric antibody. As used herein, in the term "chimeric antibody", at least portions of a variable region, namely the antigen binding region and an invariable region of the antibody (including CL1 for the light chain, and CH1, CH2, and CH3 regions for a heavy chain) are derived from different species. For example, the variable region may be mouse derived, while the invariable region may human derived. Alternatively, the chimeric antibody may refer to a class switched antibody, for example, an antibody whose type changes from an IgG type to an IgE type.

Further, the anti-CD40 antibody or antigen-binding fragment thereof according to the present disclosure may be a humanized antibody. As used herein, the term "humanized antibody" means that a backbone of the antibody is a human antibody and that a portion of the CDR region is modified to include only a part of the CDR of the species from which the original antibody molecule is derived, wherein the part is essential for specific binding to the antigen. For example, a CDR portion except a portion of CDR of monkey- or mouse-derived antibodies necessary for specific binding to the antigen, and the light and heavy chain backbones are replaced with human antibodies.

Further, according to the present disclosure, antibodies according to the present disclosure may be produced in various forms of antibodies. The antibody according to the present disclosure may be produced as a multifunctional fusion antibody such as CD40+CD40L fusion antibody by fusing Fabs having different functions. Further, a whole or intact antibody may be provided by recombination with human derived invariable regions with the light chain and heavy chain variable regions obtained from Fab antibodies.

Further, the anti-CD40 antibody or antigen-binding fragment thereof according to the present disclosure may be a monoclonal antibody. The term "monoclonal antibody" means antibody molecules of a single molecular composition obtained from substantially the same antibody population. The monoclonal antibody shows a single binding specificity and affinity to a specific epitope.

The monoclonal antibodies may be basically produced by fusion of myeloma cells with splenocytes derived from immunized mammals and may be produced using a variety of methods known in the art. In another embodiment, the antibody according to the present disclosure including an antibody fragment including one or more CDRs derived from the light chain of an antibody produced in hybridoma deposited in accession number KCLRF-BP-00336, and/or one or more CDRs derived from the heavy chain.

Antibodies according to the present disclosure may be additionally conjugated with functional substances selected from the group including therapeutic agents, prodrugs, peptides, proteins, enzymes, viruses, lipids, biological modifiers, drugs and polyethylene glycol (PEG) depending on their specific purposes. Further, depending on the type of material to be conjugated, the antibody may be produced using various methods.

The therapeutic agents, prodrugs, peptides, proteins, enzymes, viruses, lipids, biological modifiers and drugs may use any of those commonly used in the art, as long as they may achieve the desired effect.

Fragments of antibodies may be obtained with treatment using pepsin or papain. F(ab')$_2$ fragments may be obtained by treating intact antibodies with pepsin. When this is subjected to subsequent treatment using a thiol reducing agent, Fab fragments including portions of the light chain and heavy chain may be obtained. Fab fragments may be obtained by treatment of an intact antibody with papain. For example, the antibody produced in the hybridoma according to the present disclosure may be treated with pepsin or papain to prepare an antibody fragment such as F(ab')$_2$ or Fab that specifically recognizes CD40.

Fv fragments are antibody fragments composed of only variable regions of heavy and light chains. The two variable regions may be linked to each other via chemical cross-linkers or via non-covalent or covalent binding such as intermolecular disulfide binding (Inbar et al. (1972) PNAS 69:2659-2662). For example, the CD40 specific antibodies may be prepared by enzymatically treating the antibody produced in the hybridoma according to the present disclosure to isolate only the heavy and light chain variable regions, or using recombinant DNA technology.

SCA fragments may be produced by enzyme treatment or genetic engineering. In the antibody fragments in accordance with the present disclosure, the variable region of the light chain and the variable region of the heavy chain are linked by linkers such as polypeptides. The production method of ScFv may refer to, for example, those described in U.S. Pat. Nos. 4,936,778 or 5,892,019. An antibody that specifically recognizes CD40 may be prepared by enzymatically treating the antibody produced in the hybridoma according to the present disclosure or by using recombinant DNA technology, for example, producing a vector including nucleic acid sequences encoding heavy chain and/or light chain variable regions of the antibody and expressing the vector in appropriate cells.

As used herein, the term "binding" or "specific binding" refers to the affinity of an antibody or antibody composition in accordance with the present disclosure to antigen. In antigen antibody binding, "specific binding" may be distinguished from nonspecific background binding, typically where the dissociation constant (Kd) is smaller than $1 \times 10^{-5}$ M or smaller than $1 \times 10^{-6}$ M or smaller than $1 \times 10^{-7}$ M. Specific binding may be detected by methods known in the art, such as ELISA, surface plasmon resonance (SPR), immunoprecipitation, coprecipitation, and the like. Appropriate controls may be used to distinguish nonspecific binding from specific binding.

The antibody according to the present disclosure including an intact antibody or fragment thereof as described above may be present as a multimer such as a dimer, trimer, tetramer, and pentamer, including at least a portion of the antigen binding ability of the monomer. Such multimers include homomultimers, or heteromultimers. Since antibody multimers contain a large number of antigen binding regions, they have better binding ability to antigens than monomers. Multimers of antibodies are used for easy multifunctional (bifunctional, trifunctional, and tetrafunctional) antibody preparations.

As used herein, the term "multifunctional" antibody or an antibody composition refers to an antibody or an antibody composition having two or more activities or functions (e.g., antigen binding capacity, enzyme activity, ligand or receptor binding capacity). For example, the antibody according to the present disclosure may be bound to a polypeptide having enzymatic activity such as luciferase, acetyltransferase, galactosidase and the like. Multifunctional antibodies include multivalent or multispecific (bispecific, trispecific, etc.) antibodies.

The term "multispecific" antibody includes a variable region that may bind to two or more different epitopes. The two or more epitopes may exist in one antigen or in different antigens.

Further, according to another aspect according to the present disclosure, the present disclosure provides an isolated nucleic acid molecule comprising the nucleotide sequence encoding the anti-CD40 antibody or antigen-binding fragment thereof described above and provides an expression vector including the isolated nucleic acid molecule.

Nucleic acids include, for example, DNA, cDNA, RNA, or recombinant or synthesized DNA or RNA. In one embodiment, the nucleic acid molecule is cDNA. The nucleic acid may be corresponding genomic DNA or fragments thereof. The nucleic acid sequence encoding the antibody or a part or fragment thereof according to the present disclosure may vary due to the redundancy of the nucleic acid sequence encoding the amino acid. This sequence may be included in the present disclosure.

Vectors that may be used in the present disclosure include, for example, phage, plasmid, replicable or non-replicable virus or retroviral vectors. Nucleic acid molecules according to the present disclosure may be introduced into a variety of known vectors. For example, pUC-based vectors, pBluescript (Stratagene), pET-based vectors (Novagen) or pCR-TOPO (Invitrogen) vectors, and the like may be used as prokaryotic vectors. As a vector for eukaryotic cells, pREP (Invitrogen), pcDNA3 (Invitrogen), pCEP4 (Invitrogen), pMCI neo (Stratagene), pXT1 (Stratagene), pSG5 (Stratagene), EBO-pSV2neo, pBPV-1, pdBPVMMTneo, pRS Vgpt, pRSVneo, pSV2-dhfr, plZD35, pLXIN, pSIR (Clontech), pIRES-EGFP (Clontech), pEAK-10 (Edge Biosystems), pTriEx-Hygro (Novagen), and pCINeo (Promega) vectors, etc. may be used. However, the present disclosure is not limited thereto.

The vector according to the present disclosure may be introduced into a variety of known prokaryotic or eukaryotic cells by known transformation or transduction methods. Upon introduction into the cell, the vector may be inserted into the genome of the host cell or present in the form of extra chromosomes.

Prokaryotic cells that may be used include cells belonging to the *Escherichia, Bacillus, Streptomyces* and *Salmonella* family. Eukaryotic cells include mammalian cells such as Hela, HEK293, H9, Jurkat, mouse NIH3T3, C127, Cos1, Cos7 and CV1, mouse C2C12, BHK, CHO cells; fungal cells such as *Saccharomyces cerevisiae* or *Pichia pastoris*, and insect cells such as *Drosophila* S2 and *Spodoptera* Sf9, but not limited thereto.

Antibodies according to the present disclosure may be produced according to known methods using recombinant methods. In the recombinant method, the nucleic acid sequence encoding the heavy chain of the antibody according to the present disclosure and the antibody encoding the light chain of the antibody are cloned into one or two expression vectors which in turn are transferred to a eukaryotic host cell to express the antibody. Then, the antibody may be obtained from the host cell or the medium. Recombinant methods, including the preparation of the vectors, expression of proteins in cells from the prepared vectors and isolation of proteins therefrom, are known in the art and are described, for example, in Kaufman, R. J., Mol. (2000) Biotechnol. 16:151-160 and the like. The vector encoding the antibody according to the present disclosure may be expressed in a suitable host cell such as CHO cells, NS0 cells, SP2/0 cells, HEK293 cells, COS cells, yeast or *E. coli*. Antibodies may be obtained from lysate or medium of cells.

The nucleic acid sequence encoding an entirety or a fragment of the antibody according to the present disclosure may be separated from the hybridoma cells disclosed in accordance with the present disclosure in a conventional manner and then analyzed. The isolated nucleic acid sequence may then be cloned into an appropriate expression vector as described above, which in turn is delivered and implanted to HEK293 cells, CHO cells or NS0 cells that do not produce antibodies to produce recombinant antibodies in the host cell. The nucleic acid encoding the antibody or fragment thereof according to the present disclosure is introduced into an expression vector including a promoter, a translation initiation region, a 3' untranslated region, a polyadenylation signal, and a transcription termination signal. The light chain and heavy chain may be introduced in one vector or in separate vectors.

Further, according to another aspect according to the present disclosure, the present disclosure provides a method for producing an anti-CD40 antibody binding specifically to the epitope or the antigen-binding fragment thereof, the method comprising injecting the above-described anti-CD40 antibody epitope into non-human animals.

Antibodies according to the present disclosure may be present in intact cells including hybridomas, or lysates of the cells or a medium and may be purified therefrom in a partially or substantially pure form. Purification is intended to remove other by-products of cells other than antibodies, such as cell constructs, nucleic acids, proteins, etc. The purification may be done using known methods such as alkaline/SDS treatment, CsCl separation, column chromatography, agarose electrophoresis.

The hybridoma cells disclosed in accordance with the present disclosure may be cultured. Then, monoclonal antibodies may be separated from the medium of the hybridoma cells using conventional methods such as protein A-sepharose, hydroxyapatite chromatography, dialysis, or affinity chromatography.

According to still another aspect of the present disclosure, the present disclosure provides a composition for blocking CD40-CD40L signaling, the composition comprising an anti-CD40 antibody or an antigen-binding fragment thereof.

Since the composition according to the present disclosure includes the above-described anti-CD40 antibody or antigen-binding fragment thereof, the overlapping description therebetween is omitted to avoid excessive complexity of the present specification.

According to another aspect of the present disclosure, the present disclosure provides a pharmaceutical composition for the treatment or prevention of autoimmune disease or chronic inflammatory disease, the composition comprising the above-described anti-CD40 antibody or antigen-binding fragment thereof as an active ingredient.

According to another aspect of the present disclosure, the present disclosure provides a pharmaceutical composition for enhancing the therapeutic or prophylactic effect of an autoimmune disease or chronic inflammatory disease, the composition may be provided as an adjuvant therapeutic agent that may be used in combination with any therapeutic agent, such as an immunotherapeutic, that achieves the desired effect, for example, exhibits a therapeutic or prophylactic effect of an autoimmune disease or chronic inflammatory disease.

In accordance with the present disclosure, the term "adjuvant therapeutic agent" refers to an agent that may be used an auxiliary manner to enhance the effectiveness of an autoimmune disease or chronic inflammatory disease agent commonly used in the art. The use of the adjuvant therapeutic agent in accordance with the present disclosure may enhance the effectiveness of therapeutic agents by promoting the efficacy of autoimmune or chronic inflammatory diseases.

Further, the anti-CD40 antibody or antigen-binding fragment thereof according to the present disclosure may be used as an anti-drug antibody production inhibitor due to the CD40-CD40L signaling blocking effect.

As used in the present disclosure, the term "anti-drug antibody production inhibitor" refers to a substance which is administered to a patient who receives an antibody drug and produces an inhibitory antibody to the corresponding drug and thus has a drug resistance, such that the substance may inhibit the production of the inhibitory antibody to the drug, thereby inducing the effect of the drug. For example, 30% of patients receiving anti-TNF inhibitory antibodies (Humira, Ramicade, Enbrel, etc.) have drug resistance. However, when the anti-CD40 antibody or antigen-binding fragment thereof according to the present disclosure is administered thereto as an adjuvant, the anti-CD40 antibody or antigen-binding fragment thereof may inhibit antibody production against the anti-TNF-inhibiting antibodies to induce the effect of the anti-TNF-inhibiting antibodies, thus eliminating the drug resistance.

The compositions according to the present disclosure is formulated with a pharmaceutically acceptable carrier, optionally with excipients or stabilizers.

As used herein, the term "pharmaceutically acceptable carrier" refers to a physiologically compatible material, for example, any solvent, dispersing medium, coating antibacterial and antifungal agent, isotonic solution, absorption/ resorption delaying agent, and the like. In one embodiment, the carrier employs a material suitable, in particular, for injection and infusion. For example, the pharmaceutically acceptable carriers may include sterile water solutions or isotonic buffered saline or dispersions, and sterile powders for production of sterile injectable solution. Those skilled in the art will be able to select appropriate formulations depending on a type of an active ingredient included in the composition.

The pharmaceutical composition according to the present disclosure may further include lubricants, wetting agents, sweeteners, flavors, emulsifiers, suspending agents, preservatives, etc. in addition to the components. Suitable pharmaceutically acceptable carriers and formulations are described in detail in Remington's Pharmaceutical Sciences (19th ed., 1995).

The composition according to the present disclosure may be administered via various routes known in the art. It will be apparent to those skilled in the art that a mode and route of administration thereof may vary depending on a desired effect. The pharmaceutical composition according to the present disclosure may be administered orally or parenterally, preferably parenterally. When administered parenterally, the pharmaceutical composition according to the present disclosure may be administered in an intravenous, subcutaneous, intramuscular, or intraperitoneal injection manner. The route of administration of the pharmaceutical composition according to the present disclosure is preferably determined according to a type of a target disease.

An effective dosage and administration duration of the pharmaceutical composition according to the present disclosure may vary depending on a desired therapeutic effect, while considering a specific patient, a type of an antibody included in the composition, and a mode of administration in order not to cause toxicity to the patient. An actual dosage of each patient should be selected in consideration of various factors such as an activity of the composition used, a route of administration, a time duration of administration, a rate of secretion, the other drugs used together, a sex, an age, a weight, a general health state, and an underlying disease. In one embodiment, the antibody according to the present disclosure may be administered in an amount of about 1 to 100 mg/kg body weight, for example, about 10, 20, 30, 40, or 50 mg/kg body weight for the treatment or prevention of the disease. In some cases, however, the composition may be administered in an amount of about 100 mg/kg body weight.

The pharmaceutical composition according to the present disclosure may be administered at appropriate intervals, for example, daily, weekly and monthly intervals, while considering a half-life of the antibody administered.

Further, the composition according to the present disclosure may be formulated in a suitable pharmaceutically acceptable dosage form, for example, in a hydrated form, such as in an aqueous solution, or lyophilized form, regardless of the route of administration.

According to a preferred embodiment according to the present disclosure, the autoimmune disease may include diabetes mellitus type 1, alopecia greata, ankylosing spondylitis, antiphospholipid syndrome, autoimmune Addison's disease, adrenal autoimmune disease, autoimmune hemolytic anemia, autoimmune hepatitis, autoimmune ovary and testicles, autoimmune thrombocytopenia, Behcet's disease, bullous swelling, cardiomyopathy, celiac sprue-dermatitis, chronic fatigue immunodeficiency syndrome, chronic inflammatory demyelinating polyneuropathy, Churg-Strauss syndrome, scar pulmonary swelling, CREST syndrome, cold-cold aggregate disease, Crohn's disease, discus lupus, essential cryoglobulinemia, fibromyalgia-fibromyositis, glomerulonephritis, Graves' disease, Guillain-Barre Syndrome, Hashimoto's thyroiditis, idiopathic pulmonary fibrosis, idiopathic thrombocytopenic purpura, IgA neuritis, juvenile arthritis, squamous gland, lupus erythematosus, Meniere's disease, mixed connective tissue disease, multiple sclerosis, myasthenia gravis, vulgaris ulcer, pernicious anemia, crystalline polyarteritis, polychondritis, autoimmune polycystic syndrome, rheumatoid polymyalgia, polymyositis, dermatomyositis, primary agammaglobulinemia, primary biliary cirrhosis, psoriasis, psoriatic arthritis, Raynaud's phenomenon, Reiter syndrome, rheumatoid arthritis, sarcoidosis, scleroderma, stiff-man syndrome, systemic lupus erythematosus, lupus erythematosus, Takayasu's arteritis, transient arteritis, giant cell arteritis, ulcerative colitis, uveitis, vitiligo, and Wegener's granulomatosis. Most preferably, the autoimmune disease may be the diabetes mellitus type 1.

According to a preferred embodiment according to the present disclosure, the chronic inflammatory disease is selected from the group consisting of inflammatory bowel disease, Crohn's disease, ulcerative colitis, pancreatitis, chronic hepatitis, esophagitis, gastritis, colitis, pneumonia, bronchitis, sore throat, myocardial infarction, heart failure, Alzheimer's disease, psoriatic arthritis, rheumatoid arthritis, multiple sclerosis, systemic lupus erythematosus, asthma, kidney failure, psoriasis, anemia, diabetes and fibrosis.

According to another aspect of the present disclosure, the present disclosure provides a composition for inhibiting immunorejection upon organ transplantation, the composition comprising the anti-CD40 antibody or antigen-binding fragment thereof.

The composition may be used in combination with existing immunomodulators known in the art.

The transplantation includes transplanting at least one selected from the group consisting of an allogeneic cell, a xenogeneic cell, an allogeneic tissue, a xenogeneic tissue, an allogeneic organ and a xenogeneic organ.

The composition according to the present disclosure may effectively inhibit the interaction of CD40 and CD154, thereby inhibiting both T cell activation and antibody production, thereby inhibiting both cellular and humoral immune responses.

Thus, the composition inhibits or reverses the rejection of the tissue graft by the graft receptor, prolongs or preserves the function of the tissue transplanted into the graft receptor, or restores the function of the damaged graft tissue in the graft receptor.

Since the composition according to the present disclosure contains the above-described anti-CD40 antibody or antigen-binding fragment thereof, the description thereof is omitted to avoid excessive complexity of the present specification.

According to another aspect of the present disclosure, the present disclosure provides a method of treating an autoimmune disease or chronic inflammatory disease, the method comprising administering the above-described pharmaceutical composition to a subject in need of treatment.

Since the method according to the present disclosure uses the composition containing the anti-CD40 antibody or antigen-binding fragment thereof as described above, the description thereof is omitted to avoid excessive complexity of the present specification.

That is, the anti-CD40 antibody or antigen-binding fragment thereof according to the present disclosure that recognizes novel CD40 epitope according to the present disclosure and inhibits the interaction thereof with CD154, and the composition containing the same may be effectively used to block the CD40-CD154 signaling, for the treatment, prevention or control of the autoimmune disease, as well as for suppressing the immune rejection in organ transplantation.

Advantageous Effects

The novel anti-CD40 antibody according to the present disclosure directly targets not CD40 ligand but CD40 and blocks CD40-CD154 signaling without stimulating platelets to exhibit excellent antagonistic effect. Thus, the novel anti-CD40 antibody is expected to be used as an effective agent to treat the autoimmune disease and to overcome various immunorejection reactions occurring at the receptor when transplanting allogeneic or xenogeneic organs.

MODES OF THE INVENTION

Figures 1A, 1B:
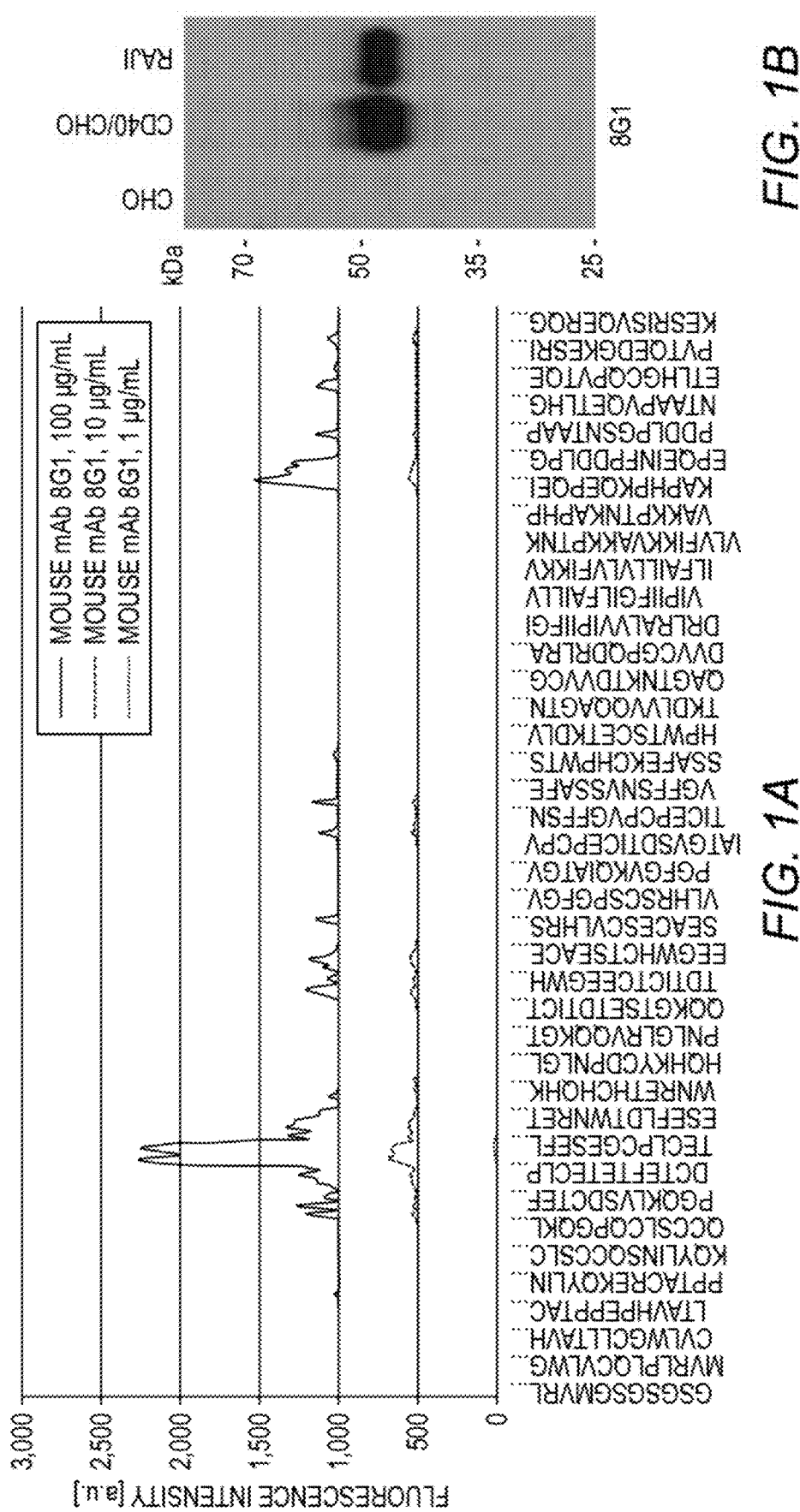
FIG. 1A and FIG. 1C show epitope analysis of the antibody in accordance with the present disclosure.
FIG. 1B shows a linear antigen epitope binding of the antibody in accordance with the present disclosure.

Hereinafter, Example is only for explaining the present disclosure in more detail. It will be apparent to those of ordinary skill in the technical field to which the present disclosure belongs that the scope of the present disclosure is not limited by these Examples in accordance with the gist of the present disclosure.

Example 1. Preparation of Hybridoma Producing Anti-CD40 Antibody According to the Present Disclosure The present inventors produced, selected, and analyzed a novel anti-CD40 antibody which targets CD40, and blocks CD40-CD154 (CD40L) signaling as follows.

To develop a novel anti-CD40 antibody, a human CD40 antigen (100 μg/mouse) or CD40 expressing CHO cell line per 6-week-old Balb/c female mouse was injected into the mouse intraperitoneal cavity (IP) three times for 3 weeks at $1 \times 10^7$ concentration. Blood samples were taken from the vein thereof to separate serum from the samples. We put the diluted serum with the CD40 expressing CHO cells into the isolated serum and reacted therebetween at 4° C. for 30 minutes. Then, 3 ml of PBS was added thereto and then centrifugation thereof was executed at 1500 rpm for 3 minutes to wash the unbound antibody. To identify the bound antibody, 200-fold diluted goat anti-Mouse Ig-FITC (Dinona) as a secondary antibody was input thereto and reaction therebetween occurred at 4° C. for 15 minutes. We washed the product with 3 ml of PBS in the same manner as above and measured the product by flow cytometry. A titer for the CD40 expressing CHO cell line was identified. when the titer of the CD40 expressing CHO cell line was identified by flow cytometry, it was identified that the CD40 expressing CHO cell line was highly positive in the serum immunizing the CD40 expressing CHO cell line.

We excised the spleen of the immunized mouse to obtain a single cell suspension. After washing the suspension twice with RPMI (GIBCO), trypan blue staining was performed by mixing 0.4% trypan blue (sigma) therewith at 1:1 (v/v). Then, we measured unstained cells under a microscope to count the number of the cells. X63 mouse myeloma cell line (ATCC CRL-1580) was used as cell fusion partner cells. After washing the partner cells in the same manner as the splenocytes, the number of the cells was counted.

The myeloma cells and splenocytes were mixed with each other at a ratio of 1:5 and the supernatant was removed after centrifugation of the mixture. 1 ml of 50% PEG (polyethylene glycol) 1500 previously preheated to 37° C. was slowly added thereto over 1 minute. After holding the mixture for about 1 minute, the RPMI medium was gradually added thereto and thus the mixture was diluted. After centrifugation of the mixture, the mixture was suspended in RPMI (20% FBS, hypoxanthine-aminopterin-thymidine) containing 1×HAT. We dispenses the suspension, at 150 μl/well, onto 96-well plates and incubated the cells in 37° C. 5% $CO_2$ incubator. After the fusion, we executed HAT feeding thereto for a period of time. When the wells that formed the colonies were observed, 150 μl of HT medium was added thereto, followed by 48 hours of incubation in a 37° C. 5% $CO_2$ incubator, followed by fluorescence staining. The cells were analyzed by flow cytometry. 100 μl of the hybridoma culture supernatant was added to the CD40 expressing CHO cell line, followed by reaction at 4° C. for 30 minutes. Then, 3 ml of PBS was added thereto. After centrifugation thereof at 1500 rpm for 3 minutes, the non-binding antibody was washed. To identify the bound antibody, 200-fold diluted goat anti-Mouse Ig-FITC (Jackson Laboratory) as a secondary antibody was added thereto, followed by reaction at 4° C. for 15 minutes, then, followed by washing with PBS 3 ml in the same manner as above. The cells were measured by flow cytometry.

In the above method, a monoclonal antibody that is negative to CHO cells and negative to all of normal lung cell line L132 and granulocytes and lymphocytes and monocytes of peripheral blood is selected. Finally, RM8G1 hybridoma cells of a single colony were obtained using limiting dilution.

The hybridoma was selected as the optimal hybridoma and labeled as RM8G1.

The hybridoma RM8G1 was deposited on Korean Cell Line Bank on Jan. 14, 2015. A following accession number has been assigned: KCLRF-BP-00336.

Example 2. Sequence of Anti-CD40-Antibody According to the Present Disclosure

The present inventors cloned nucleic acids encoding heavy and light chain fragments from hybridomas producing anti-CD40 antibodies to analyze the structure of antibodies produced according to the present disclosure.

Cloning and sequence determination were made as follows.

When using the RNA miniprep kit (Qiagen) according to the producer's method for cloning the gene, RNA was extracted from RM8G-1 hybridoma cells obtained in Example 1, and then PCR was performed to synthesize cDNA.

PCR conditions and cloning methods for the synthesis of heavy chain cDNA and light chain cDNA are as follows:

The CD40 antigen-specific antibody and RM8G-1 antibody gene were cloned using Mouse Ig-Primer Set (Millipore, Cat. #: 69831). PCR was performed on RNA isolated from RM8G-1 hybridoma using Mouse Ig-Primer Set. The PCR result was inserted into a pGem-T vector (Promega, Cat. #: A3600), and then the DNA sequence was identified using sequencing. Mouse antibody genes were identified using the IMGT site (www.imgt.org).

The sequences of the light chain variable regions CDRLs 1, 2 and 3 are represented by SEQ ID NOs: 3 to 5, respectively.

The sequences of the heavy chain variable regions CDRHs 1, 2 and are represented by SEQ ID NOs: 6 to 8, respectively.

Example 3. Determination of CD40 Antigen Epitope Recognized by Anti-CD40 Antibody According to the Present Disclosure The present inventors identified human CD40 antigen epitopes recognized by the anti-CD40 antibodies according to the present disclosure.

For epitope mapping, 277 peptides composed of 15 amino acids among the amino acid sequences of the human CD40 antigen were prepared and then the peptide microarray was performed using the prepared 277 peptides. One peptide is composed of 15 amino acids, 14 of which were duplicated. Since the peptide microarray plate was prepared in a duplicated manner, 78 negative control peptide spots which may not react with the total 554 peptide spots were prepared. One peptide microarray plate reacted with goat anti-IgG (H+L) Dylight680 antibody (1:5000) and we identified whether background reaction occurs. The other three microarray plates reacted with RM8G-1 at concentrations of 1 µg/ml, 10 µg/ml and 100 µg/ml, followed by washing, and then followed by reaction with goat anti-mouse IgG (H+L) Dylight680 (1:5000) at room temperature for 45 minutes. The microarray spots were read out with the LI-COR. Odyssey imaging System. When the microplate was reacted with secondary goat anti-mouse IgG (H+L) DyLight680, nonspecific binding to CD40 peptide did not occur. However, in the sample treated with RM8G-1 at a varying concentration, the binding reaction occurred as shown in FIG. 1A. The antibody RM8G-1 reacted, in the strongest level, with the ECLPCGESEF (SEQ. ID NO:9) region, and an additional weak reaction was seen in EPOEINFPDD (SED ID NO:10).

Figure 1C:
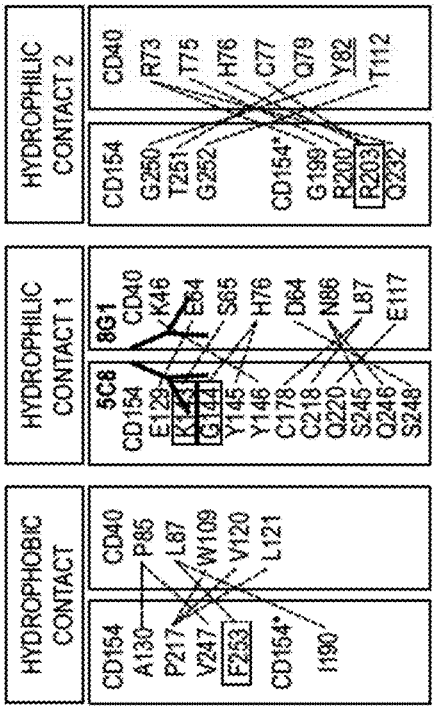
Figure 1C:
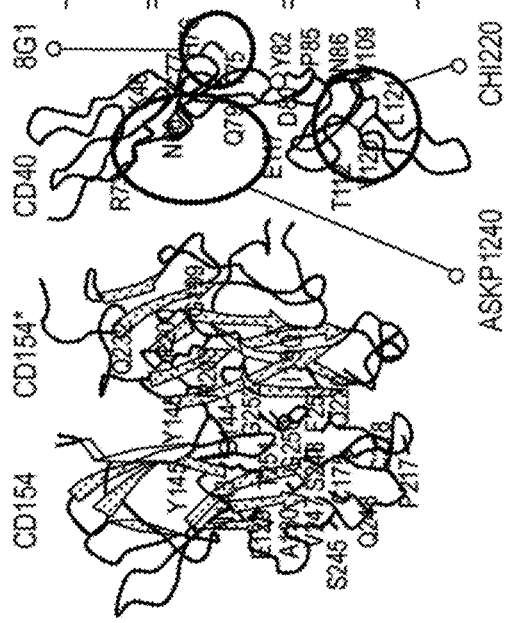

As a result, as shown in FIG. 1A to FIG. 1C, it was identified that the CD40 monoclonal antibody according to the present disclosure binds to a new epitope that is different from an antigen binding epitope to which the existing antibody as commonly used binds. The epitope sequence is as follows: ECLPCGESEF (Glu Cys Len Pro Cys Gly Glu Ser Glu Phe (SEQ ID NO:9)).

Western blot analysis was performed to determine whether RM8G-1 binds to the linear antigen epitope. That is, Raji cells were lysed with RIPA lysis buffer and electrophoresed and transferred to PVDF.

Reaction thereof with anti-CD40 RM8G-1 at 4° C. was executed overnight and reaction thereof with anti-mouse IgG-HRP (1:2000) was executed for 1 hour, then the reaction product was washed with TBST to identify color development thereof.

As a result, as shown in FIG. 1B, it was identified that the anti-CD40 antibody according to the present disclosure exhibits linear antigen epitope binding characteristics in addition to the structural form of the epitope, unlike the conventional anti-CD40 antibody.

In other words, the antigen was produced in a linear form, and, then, the Western blotting was carried out. Thus, the reaction presence indicates that the anti-CD40 antibody according to the present disclosure may recognize the linear epitope. Therefore, this is an important feature that the anti-CD40 antibody (RM8G1) according to the present disclosure recognizes the linear epitope which the conventional antibodies do not recognize.

Example 4. Antagonistic Effect of Anti-CD40 Antibodies in Accordance With the Present Disclosure The present inventors identified the antagonistic effect of the novel anti-CD40 antibody according to the present disclosure prepared in Example 1.

4-1. Inhibition of CD40-CD154 Signaling by Anti-CD40 Antibodies According to the Present Disclosure The present inventors identified the ability to inhibit CD40-CD154 signaling by the anti-CD40 antibody (RM8G-1) according to the present disclosure.

To identify the signaling inhibitory effects of RM8G-1, PBMC was isolated from the blood of rhesus monkey as a primate, and His-tag CD40L was reacted therewith. At this time, the reaction product was treated with RM8G-1 at a varying concentration, and they reacted at room temperature for 30 minutes. After washing, flow cytometry was performed by ice reaction thereof with anti-histidine-FITC antibody for 40 minutes. After flow cytometry, FITC expression is indicated as a mean-fluorescence intensity value. The higher this value, the lower the blocking effect. The relative inhibition was expressed as a relative value of the M.F.I value of the experimental group, while a M.F.I value of the group not treated with RM8G-1 is set to 100.

Further, to determine whether RM8G-1 blocks the human CD40-CD40L signaling, Ramos B cells and CD40L-expressed CHO cells (CHO-CD40L) were co-cultured for 24 hours. At this time, the cultures were treated with RM8G-1 at a varying concentration (0.1, 0.5, 1, 2.5, 5, 10 and 20 µg/ml).

In the Ramos B cells, CD40 is expressed and thus the Ramos B cells are stimulated and activated by the CD40L signal of CHO-CD40L. The activated Ramos cells express an adhesion factor called ICAM-1. Thus, the degree of blocking by RM8G-1 may be quantified by identifying the expression level of the ICAM-1 by flow cytometry.

That is, the Ramos, and CHO-CD40L which were cultured and were not treated with the RM8G-1 were defined as positive control groups. In the groups, a degree (indicated by MFI) of expression of ICAM-1 expressed in Ramos acted at a reference. Thus, the inhibition ability was calculated by comparing the expression level of ICAM-1 as identified in the antibody-treated group with the reference.

Figure 2A:
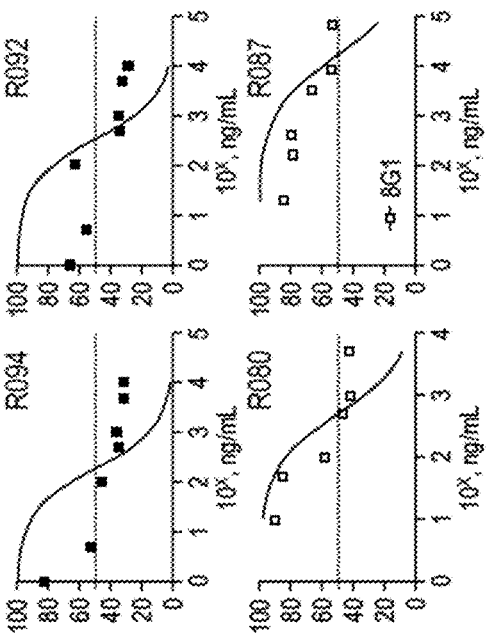
FIG. 2A and FIG. 2B show high efficiency of blocking CD40-CD154 signaling by the antibody in accordance with the present disclosure.
Figure 2B:
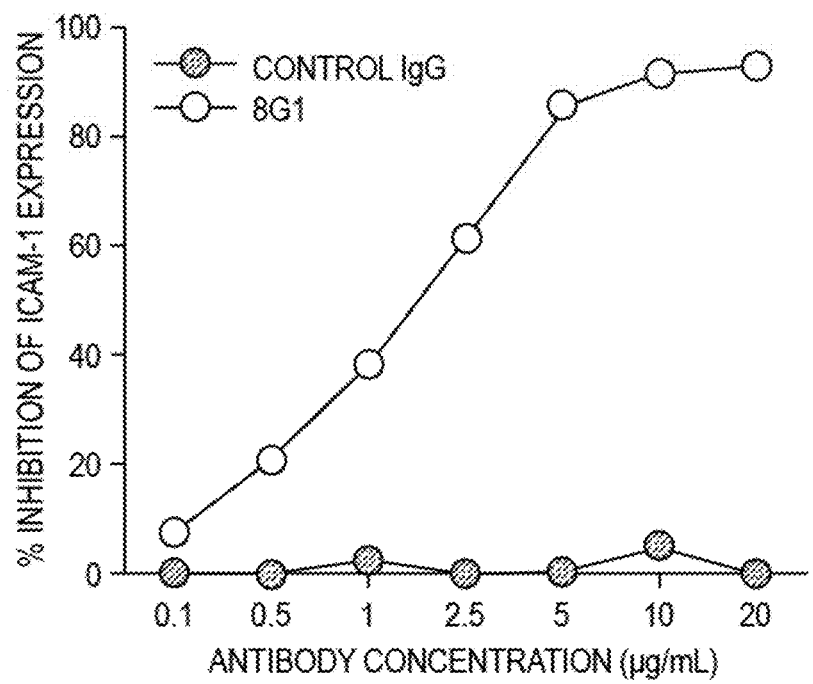

As a result, as shown in FIG. 2A and FIG. 2B, in primates and humans, the anti-CD40 antibody (RM8G-1) according to the present disclosure may not only specifically inhibit CD40-CD154 binding, but also inhibit CD40-CD154 signaling at a high efficiency.

4-2. Affinity of Anti-CD40 Antibody According to the Present Disclosure to CD40 Antigen The present inventors identified the affinity of the anti-CD40 antibody (RM8G-1) according to the present disclosure to a human CD40 antigen.

100 ng of human CD40 antigen per well was added to a Maxisrop ELISA plate and reacted at 37° C. for 1 hour to coat the antigen. Then, 200 µl of 1× blocking solution (sigma) per well was added thereto and they reacted at 37° C. for 1 hour for blocking. Onto the prepared plate, the RM8G-1 antibody and 100 µl PBS were added, and then they reacted for 1 hour at 37° C. and washed with PBS to remove the non-binding antibody. In this connection, the RM8G-1 antibody was serially diluted in multiples of 3 while starting at a concentration of 50 µg/ml. Thus, a total of 12 points of RM8G-1 antibody bindings occurred in a range from 50 µg/ml to 0.000282 µg/ml. After diluting Goat anti-Mouse IgG-HRP (Jackson Laboratory) and adding the diluted Goat anti-Mouse IgG-HRP thereto, they reacted with each other for 30 minutes. After washing the reaction product with PBS, 50 µl of TMB solution per well was added thereto and they reacted with each other for 10 minutes, and then 50 µl of sulfuric acid was added thereto to stop the reaction. The absorbance was measured at 450 nm.

Figure 3:
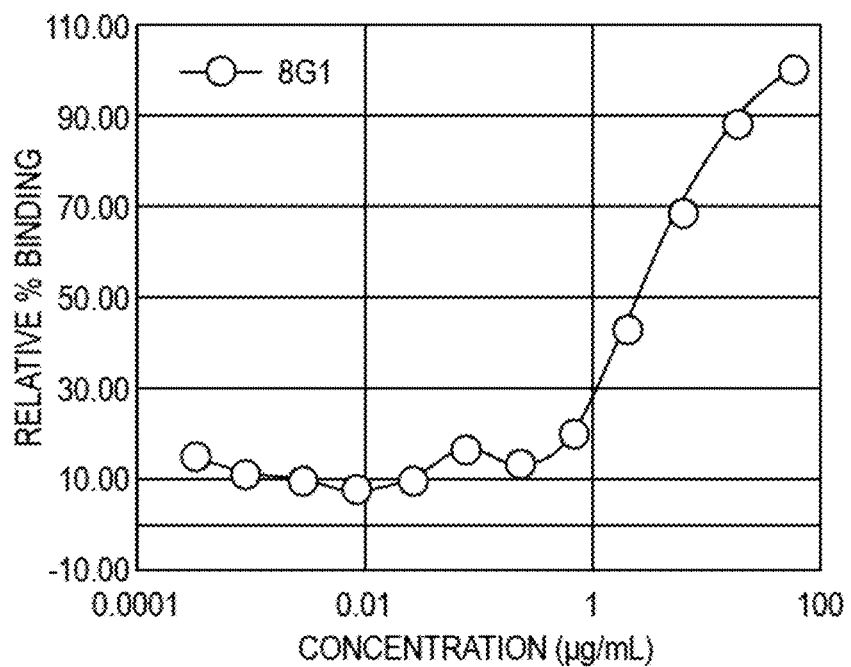
FIG. 3 shows high affinity of the antibody in accordance with the present disclosure.

As a result, as shown in FIG. 3, when the affinity thereof to the CD40 antigen was identified using the ELISA method, the result indicates that the RM8G-1 antibody binds to the CD40 antigen according to the concentration gradient.

Therefore, the anti-CD40 antibody (RM8G-1) according to the present disclosure shows excellent affinity.

Association rate constant Ka, dissociation rate constant Kd and equilibrium dissociation constant KD values were identified using a CM5 sensor chip assay to identify the high affinity of the RM8G-1 antibody to CD40.

That is, the anti-His antibody was immobilized on the surface of the CM5 sensor chip by an amine coupling method. His-tagged CD40 antigen was captured by reacting the His-tagged CD40 antigen with the antibody and then the captured antigen was reacted with sensor chip coated with an anti-his antibody. The results were read using biocore T200 (GE Healthcare).

As a result, the anti-CD40 antibody (RM8G-1) according to the present disclosure showed $Ka=4.741\times105$ $M^{-1}S^{-1}$, $KD=2.340\times10^{-4}S^{-1}$, Equilibrium Dissociation Constant $KD=4.936\times10^{10}M$. This suggests that the anti-CD40 antibody (RM8G-1) has high affinity at which the anti-CD40 antibody (RM8G-1) may be developed into a therapeutic agent without additional affinity maturation.

4-3. Non-Agonistic Properties of Anti-CD40 Antibodies According to the Present Disclosure The anti-CD40 antibody that recognizes CD40 has been disclosed to exhibit various biological activities against B cells. Based on the interaction with CD40 and CD40L, the anti-CD40 antibody is largely divided to be agonistic and antagonistic.

Agonistic anti-CD40 antibodies may be effective in the treatment of diseases that require the activation of interactions thereof with CD40 and CD40L and is known to be used for the treatment of infectious diseases such as bacteria and viruses, and cancer treatment.

However, because there are reports that CD40L is expressed in activated platelets (V. Henn et. al., Nature 391:591, 1998), the use of the anti-CD40L antibodies as therapeutic agents has been reported to present a risk of causing blood clots (T. Kawai et. al., Nat. Medi. 6:114, 2000).

Further, CD40 has been reported as a B cell receptor that allows malignant tumor B cells such as non-Hodgkin's vesicular lymphoma to activate and survive (Johnson et al., Blood 82:1848-1857 (1993); and Metkar et al. Cancer Immunol. Immunother. 47:104 (1998).

In view of this fact, the antibody against CD40 rather than the anti-CD40L antibody may be more safely used as an antibody therapeutic drug which inhibits binding of CD40 and its ligand. Therefore, the anti-CD40 antibody should inhibit the binding of CD40L to CD40, and should not activate CD40.

CD40 plays an important role in the immune response. Thus, inhibiting the binding of CD40 and its ligand may achieve immunosuppression during organ transplantation or treat the autoimmune disease.

Therefore, the present inventors identified the non-agonistic properties of the anti-CD40 antibody (RM8G-1) according to the present disclosure.

Ramos (B cell) cells were cultured on a plate coated with RM8G-1 at a varying concentration. At this time, the agonistic antibody stimulates CD40 of Ramos cells, which causes signal transduction and the CD40 activation. Thus, the expression of the adhesion factor, that is, ICAM-1 is increased. However, it has been identified that RM8G-1 does not cause the CD40 activation.

Figure 4:
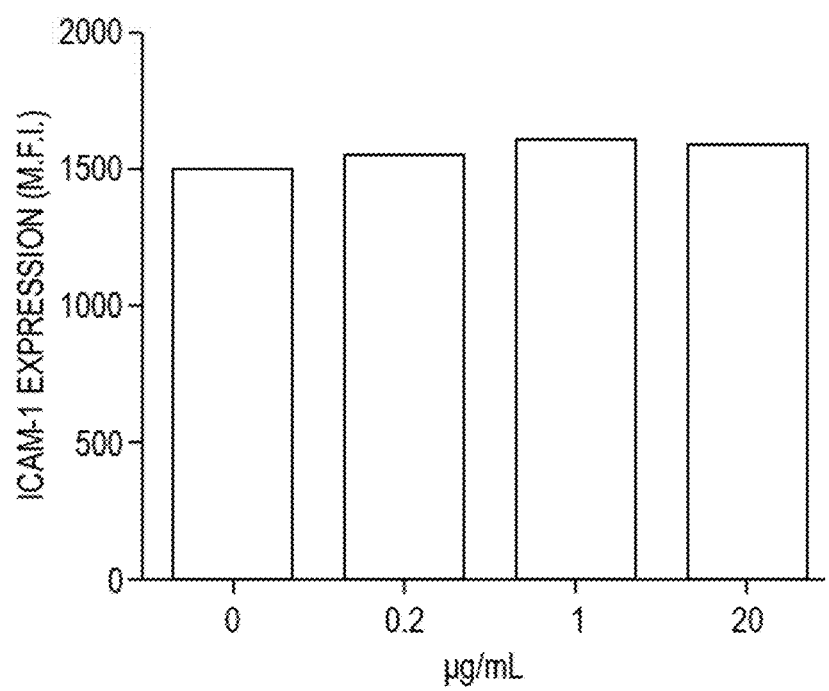
FIG. 4 shows non-agonistic properties of the antibody in accordance with the present disclosure.

As a result, as shown in FIG. 4, it was identified that the anti-CD40 antibody (RM8G-1) according to the present disclosure is a good non-agonistic antibody.

Therefore, the anti-CD40 antibody according to the present disclosure (RM8G-1) is an antagonistic anti-CD40 antibody that maintains non-agonistic and antagonistic activity and thus is more effective in treatment of the autoimmune disease or suppressing of rejection in transplantation of organs, bone marrow and the like.

4-4. Cytotoxic Effector Function of Anti-CD40 Antibody According to the Present Disclosure The present inventors have further produced the antagonistic anti-CD40 antibody (RM8G-1) according to the present disclosure into the non-depleting or minimal-depleting antibody using Fc-engineering.

The Fc engineering of the anti-CD40 antibody is intended to eliminate the side effects of depletion of target cells (primarily, antigen-delivered cells) due to cytotoxicity such as ADCC and CDC when developing the antibodies as therapeutics. In order to eliminate the ADCC or CDC, it is possible to modify the region of the antibody bound to the Fc receptor of the cell or the complement, or use a low binding ability based IgG4 Fc.

Specifically, the present inventors identified functions of cytotoxic effector such as antibody dependent cell-mediated cytotoxicity (ADCC) and/or complement dependent cytotoxicity (CDC) of the antagonistic anti-CD40 antibody (RM8G-1) according to the present disclosure.

For CDC assay, Raji cells as human B cell lines were dispensed onto 96-well plates at $5\times10^4$ cells/well and incubated in 37° C. $CO_2$ incubator for 20 to 24 hours. After replacing the culture medium in each well with RPMI medium containing no fetal calf serum, purified RM8G-1 and Rituximab antibodies were mixed with 10% human serum to reach a final concentration of 10 µg/ml and 1 µg/ml respectively, and then 100 µl thereof were dispensed into the wells. After 4 and 21 hours, the cells were stained with anti-CD19 antibody-PE-Cy7 (BD) as a marker for detecting Raji cells and with 7-AAD (BD) as a reagent for identifying whether cells survived. Analysis was performed by flow cytometry. A group that is both CD19 positive and 7-AAD positive was compartmentalized. CDC of Raji cells was analyzed. The results are shown in FIG. 5A.

For ADCC assays, Raji cells, as human B cell lines, are dispensed, at $5 \times 10^4$ cells/well, onto 24 well plates and incubated for 20 to 24 hours in a 37° C. $CO_2$ incubator. After replacing the culture medium of each well with RPMI medium containing no fetal calf serum, human PBMC as effector cells was added thereto such that the number of human PBMC is 100 times ($5 \times 10^6$ cells/well) of the number of the target cell Raji cells. RM8G-1 and Rituximab antibodies were dispensed on the plates to reach final concentrations of 10 μg/ml, 1 μg/ml and 0.1 μg/ml. After 4 and 21 hours, the cells were stained with anti-CD19 antibody-PE-Cy7 (BD) as a marker for detecting Raji cells and with 7-AAD (BD) as a reagent for identifying whether cells survived. Analysis was performed by flow cytometry. A group that is both CD19 positive and 7-AAD positive was compartmentalized. Cytotoxicity results of Raji cells were analyzed. The results are shown in FIG. 5B.

At this time, Rituxan (Rituximab) as an anti-CD20 antibody known in the art, was used as a control.

Figures 5A, 5B:
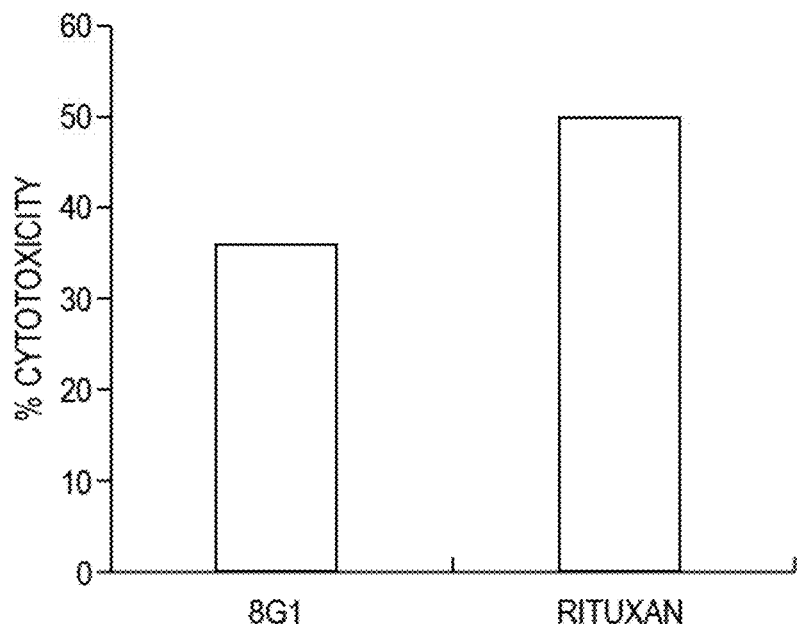
FIG. 5A and FIG. 5B show properties of a cytotoxic effector (minimal depleting) of the antibody in accordance with the present disclosure.

As a result, as shown in FIG. 5A and FIG. 5B, the anti-CD40 antibody (RM8G-1) according to the present disclosure does not exhibit cellular cytotoxicity such as ADCC and exhibits minimal CDC, compared to known antibodies. Minimal CDC may be overcome by using Fc variants or Fc in an IgG4 form without CDC or ADCC for future humanized antibody preparations.

Example 5. Species Cross-Reactivity of Anti-CD40 Antibodies According to the Present Disclosure The present inventors performed FACS analysis to determine the binding and affinity of the antibody according to the present disclosure to CD40 from various species, particularly primate monkeys.

Monkey CD40-CHO cells obtained by transforming Monkey CD40 gene in Chinese hamster ovary cell (CHO) cells were prepared. Raji cells are human cell lines. The RM8G-1 antibody (0.5 μg/ml) was reacted with CHO cells, Monkey CD40-CHO cells, and Raji cells for 30 minutes on ice and the reaction product was washed and then reacted with anti-mouse IgG-PE for 40 minutes on ice. After washing, flow cytometry was performed. CHO was used as a negative control and Raji was used as a positive control.

Figure 6:
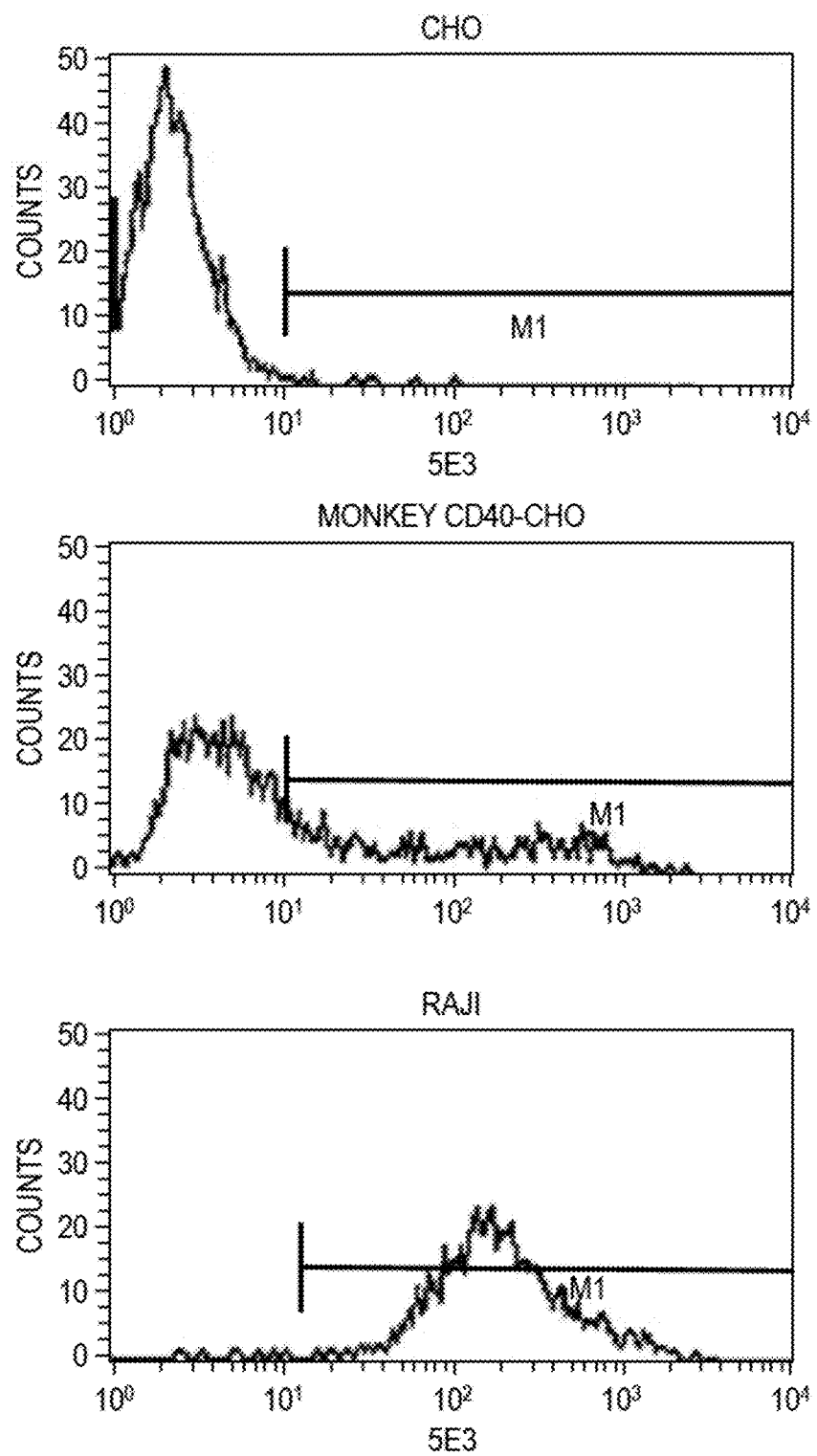
FIG. 6 shows primate/human cross reactions of the antibody in accordance with the present disclosure.

As a result, as shown in FIG. 6, the anti-CD40 antibody according to the present disclosure may cross-bind with CD40 of primates (Rhesus monkey) and human. This suggests that the anti-CD40 antibody according to the present disclosure is very advantageously used for preclinical research and therapeutic development.

Example 6. Blocking Xenogeneic Cell Signaling by Anti-CD40 Antibody According to the Present Disclosure The present inventors identified the xenogeneic cell (pig) signaling blocking effect by the anti-CD40 antibody according to the present disclosure.

In order to identify whether the anti-CD40 antibody according to the present disclosure blocks CD40 signaling in the xenogeneic cells (pigs), PBMCs were isolated from pig blood and reacted with CD40L-His tag on ice for 1 hour. At this time, the reaction product was treated with RM RM8G-1 at a varying concentration to identify the pig CD40-CD40L signaling blocking effect using flow cytometry. For this purpose, the reaction of the treated cells with anti-His tag-FITC antibody was carried out for 40 minutes and then the amount of CD40L-Hig tag that reacted with CD40 of swine PBMC was expressed as a mean-fluorescence intensity.

Figure 7:
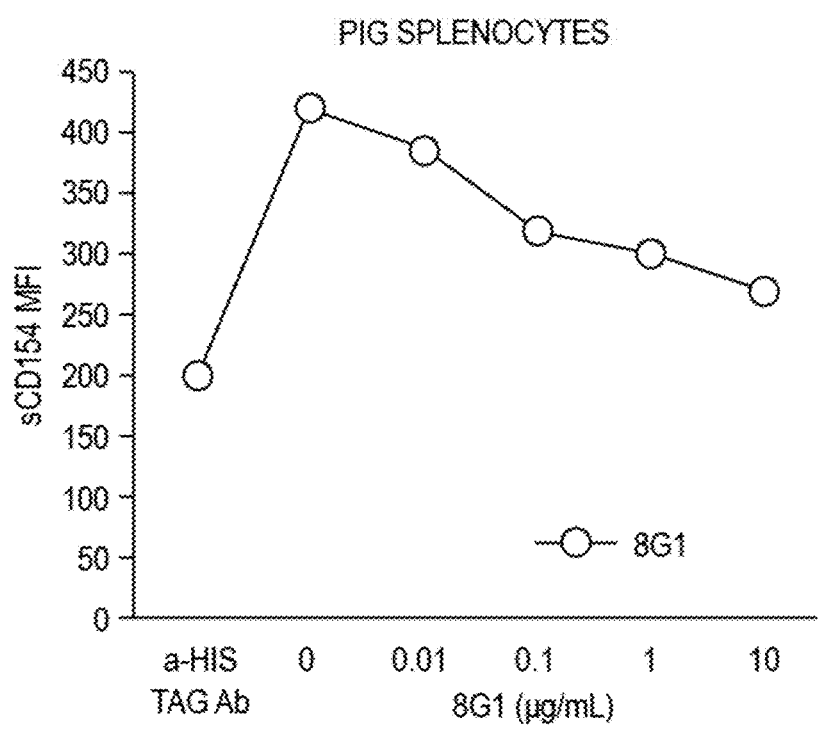
FIG. 7 shows that the antibody in accordance with the present disclosure blocks porcine CD40-CD40L binding.

As a result, as shown in FIG. 7, the anti-CD40 antibody according to the present disclosure blocked the swine CD40-CD40L binding in proportion to the concentration. Thus, the anti-CD40 antibody according to the present disclosure is only an antibody to block the CD40-CD154 signaling of the donor-receptor that occurs during xenogeneic cell/xenogeneic solid organ/xenogeneic islet transplantation and may be expected to be very effective in suppressing rejection in xenogeneic transplantation.

In conclusion, the present disclosure provides a novel antibody (RM8G-1) that tray bind to the epitope (ECLPCGESEF (SEQ ID NO:9)) of human CD40 and inhibit CD40-CD154 interaction. The efficiency of blocking the human CD40-CD154 binding by the novel antibody was found to be more excellent than the conventional anti-CD40 antibody.

Further, the present disclosure provides the anti-CD40 antibody (RM8G-1) which meets all the prerequisites to be an anti-CD40 antibody for autoimmune disease treatment and for suppressing of immune rejection in organ transplantation, and thus is used for excellent autoimmune disease treatment agent and immunosuppressive agent in organ transplantation.

The invention claimed is:

1. An isolated anti-CD40 antibody or an antigen-binding fragment thereof, wherein the anti-CD40 antibody or the antigen-binding fragment thereof specifically binds to an epitope consisting of ECLPCGESEF (SEQ ID NO:9) of human CD40 amino acid sequences:
wherein the anti-CD40 antibody or antigen-binding fragment thereof is produced by a hybridoma cell line deposited in accession number KCLRF-BP-00336.

2. The isolated anti-CD40 antibody or antigen-binding fragment thereof of claim 1, wherein the anti-CD40 antibody or antigen-binding fragment thereof comprises:
an immunoglobulin light chain variable region (VL) composed of an amino acid sequence set forth in SEQ. ID NO: 1; and
an immunoglobulin heavy chain variable region (VH) composed of an amino acid sequence set forth in SEQ ID NO: 2.

3. An isolated anti-CD40 antibody or antigen-binding fragment thereof, wherein the anti-CD40 antibody or antigen-binding fragment thereof comprises an immunoglobulin light chain variable region (VL) comprising amino acid sequences of LCDR1 set forth in SEQ ID NO: 3, LCDR2 set forth in SEQ ID NO: 4 and LCDR3 set forth in SEQ ID NO: 5 as a complementarity-determining region (CDR) sequence,
and comprises an, immunoglobulin heavy chain variable region (VH) comprising amino acid sequences of HCDR1 set forth in SEQ ID NO: 6, HCDR2 set forth in SEQ ID NO: 7 and HCDR3 set forth in SEQ ID NO: 8 as a complementarity-determining region (CDR) sequence.

4. The isolated anti-CD40 antibody or antigen-binding fragment thereof of claim 1, wherein the anti-CD40 antibody is selected from the group consisting of monoclonal antibody, chimeric antibody, primatized antibody, humanized antibody, and human antibody.

5. The isolated anti-CD40 antibody or antigen-binding fragment thereof of claim 1, wherein the anti-CD40 antibody is selected from the group consisting of multimeric antibodies, heterodimeric antibodies, semi-dimeric antibodies, tetravalent antibodies, bispecific antibodies and single-chain antibodies.

6. The isolated anti-CD40 antibody or antigen-binding fragment thereof of claim 1, wherein the antigen-binding fragment is selected from the group consisting of Fab, F(ab)$_2$, Fab', F(ab')$_2$, F(ab')$_3$, Fd, Fv, and a domain antibody.

7. The isolated anti-CD40 antibody or antigen-binding fragment thereof of claim 1, wherein the anti-CD40 antibody or antigen-binding fragment thereof is further conjugated with a substance selected from the group consisting of a therapeutic agent, a prodrug, peptide, protein, enzyme, virus, lipid, a biological modifier, a drug and PEG.

8. The isolated anti-CD40 antibody or antigen-binding fragment thereof of claim 1, wherein the anti-CD40 antibody or antigen-binding fragment thereof blocks CD40-CD40L signaling.

9. A method for blocking CD40-CD40L, signaling in a subject with autoimmune disease, the method comprising administering the anti-CD40 antibody or antigen-binding fragment thereof of claim 1 to a subject in need thereof.

10. The method of claim 9, wherein the autoimmune disease is selected from the group consisting of diabetes mellitus type 1, alopecia greata, ankylosing spondylitis, antiphospholipid syndrome, autoimmune Addison's disease, adrenal autoimmune disease, autoimmune hemolytic anemia, autoimmune hepatitis, autoimmune ovary and testicles, autoimmune thrombocytopenia, Behcet's disease, bullous swelling, cardiomyopathy, celiac sprue, dermatitis, chronic fatigue immunodeficiency syndrome, chronic inflammatory; demyelinating polyneuropathy, Churg-Strauss syndrome, scar pulmonary swelling, CREST syndrome, cold-cold aggregate disease, Crohn's disease, discus lupus, essential cryoglobulinemia, fibromyalgia-fibromyositis, glomerulonephritis, Graves' disease, Guillain-Barre Syndrome, Hashimoto's thyroiditis, idiopathic pulmonary fibrosis, idiopathic thrombocytopenic purpura, IgA neuritis, juvenile arthritis, squamous gland, lupus erythematosus, Meniere's disease, mixed connective tissue disease, multiple sclerosis, myasthenia gravis, vulgaris ulcer, pernicious anemia, crystalline polyarteritis, polychondritis, autoimmune polycystic syndrome, rheumatoid polymyalgia, polymyositis, dermatomyositis, primary agammaglobulinemia primary biliary cirrhosis, psoriasis, psoriatic arthritis, Raynaud's phenomenon, Reiter syndrome, rheumatoid arthritis, sarcoidosis, scleroderma, stiff-man syndrome, systemic lupus erythematosus, lupus erythematosus, Takayasu's arteritis, transient arteritis, giant cell arteritis, ulcerative colitis, uveitis, vitiligo, and Wegener's granulomatosis.

11. A method for blocking CD40-CD40L signaling in a subject with chronic inflammatory disease, the method comprising administering the anti-CD40 antibody or antigen-binding fragment thereof of claim 1 to a subject in need thereof.

12. The method of claim 11, wherein the chronic inflammatory disease is selected from the group consisting of inflammatory bowel disease, Crohn's disease, ulcerative colitis, pancreatitis, chronic hepatitis, esophagitis, gastritis, colitis, pneumonia, bronchitis, sore throat, myocardial infarction, heart failure, Alzheimer's disease, psoriatic arthritis, rheumatoid arthritis, multiple sclerosis, systemic lupus erythermatosus, asthma, kidney failure, psoriasis, anemia, diabetes and fibrosis.

13. A method for inhibiting immunorejection in transplantation, the method comprising administering the anti-CD40 antibody or antigen-binding fragment thereof of claim 1 to a subject in need thereof.

14. The method of claim 13, wherein the transplantation includes transplanting at least one selected from the group consisting of an allogeneic cell, a xenogeneic cell, an allogeneic tissue, a xenogeneic tissue, an allogeneic organ and a xenogeneic organ.

15. The method of claim 13, wherein the method inhibits or reverses rejection of a tissue graft by a graft receptor, prolongs or preserves a function of a tissue transplanted into a graft receptor, or restores a function of a damaged graft tissue in a graft receptor.

* * * * *

UNITED STATES PATENT AND TRADEMARK OFFICE
CERTIFICATE OF CORRECTION

PATENT NO. : 11,242,397 B2
APPLICATION NO. : 16/618736
DATED : February 8, 2022
INVENTOR(S) : Park et al.

Page 1 of 1

It is certified that error appears in the above-identified patent and that said Letters Patent is hereby corrected as shown below:

In the Specification

Column 17, Line 19: Please correct "2 and are" to read -- 2 and 3 are --

Column 17, Line 53: Please correct "EPOEINFPDD" to read -- EPQEINFPDD --

In the Claims

Column 27, Line 14, Claim 2: Please correct "SEQ. ID" to read -- SEQ ID --

Column 27, Line 27, Claim 3: Please correct "an, immunoglobulin" to read -- an immunoglobulin --

Column 27, Line 36, Claim 4: Please correct "primatized" to read -- primateized --

Column 27, Line 58, Claim 9: Please correct "CD40-CD40L, signaling" to read -- CD40-CD40L signaling --

Column 28, Line 11, Claim 10: Please correct "inflammatory;" to read -- inflammatory --

Signed and Sealed this
Seventeenth Day of May, 2022

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 111
<212> TYPE: PRT
<213> ORGANISM: Artificial
<220> FEATURE:
<223> OTHER INFORMATION: VL of RM8G-1

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ala Tyr Ser Tyr Met His Trp Tyr Gln Gln Lys Pro Gly Gln Pro Pro
```

```
                35                  40                  45
Lys Leu Leu Ile Tyr Leu Ala Ser Asn Leu Glu Ser Gly Val Pro Ala
            50                  55                  60

Arg Phe Ser Gly Ser Gly Ser Gly Thr Asp Phe Thr Leu Asn Ile His
65                  70                  75                  80

Pro Val Glu Glu Asp Ala Ala Thr Tyr Tyr Cys Gln His Ser Trp
                85                  90                  95

Asp Leu Pro Tyr Thr Phe Gly Gly Thr Lys Leu Glu Ile Lys
            100                 105                 110
```

<210> SEQ ID NO 2
<211> LENGTH: 117
<212> TYPE: PRT
<213> ORGANISM: Artificial
<220> FEATURE:
<223> OTHER INFORMATION: VH of RM8G-1

<400> SEQUENCE: 2

```
Leu Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Gly Trp Ile Arg Gln Pro Pro Gly Lys Asp Leu Glu Trp Leu
        35                  40                  45

Gly Val Met Trp Gly Gly Gly Arg Thr Tyr Tyr Asn Ala Pro Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Val
                85                  90                  95

Lys Thr Gly Gln Asp Tyr Ala Val Asp Tyr Trp Gly Gln Gly Thr Ser
            100                 105                 110

Val Thr Val Ser Ser
        115
```

<210> SEQ ID NO 3
<211> LENGTH: 10
<212> TYPE: PRT
<213> ORGANISM: Artificial
<220> FEATURE:
<223> OTHER INFORMATION: LCDR1 of RM8G-1

<400> SEQUENCE: 3

```
Lys Ser Val Ser Thr Ser Ala Tyr Ser Tyr
1               5                   10
```

<210> SEQ ID NO 4
<211> LENGTH: 3
<212> TYPE: PRT
<213> ORGANISM: Artificial
<220> FEATURE:
<223> OTHER INFORMATION: LCDR2 of RM8G-1

<400> SEQUENCE: 4

```
Leu Ala Ser
1
```

<210> SEQ ID NO 5
<211> LENGTH: 9
<212> TYPE: PRT
<213> ORGANISM: Artificial

```
<220> FEATURE:
<223> OTHER INFORMATION: LCDR3 of RM8G-1

<400> SEQUENCE: 5

Gln His Ser Trp Asp Leu Pro Tyr Thr
1               5

<210> SEQ ID NO 6
<211> LENGTH: 8
<212> TYPE: PRT
<213> ORGANISM: Artificial
<220> FEATURE:
<223> OTHER INFORMATION: HCDR1 of RM8G-1

<400> SEQUENCE: 6

Gly Phe Ser Leu Thr Asp Tyr Gly
1               5

<210> SEQ ID NO 7
<211> LENGTH: 7
<212> TYPE: PRT
<213> ORGANISM: Artificial
<220> FEATURE:
<223> OTHER INFORMATION: HCDR2 of RM8G-1

<400> SEQUENCE: 7

Met Trp Gly Gly Gly Arg Thr
1               5

<210> SEQ ID NO 8
<211> LENGTH: 11
<212> TYPE: PRT
<213> ORGANISM: Artificial
<220> FEATURE:
<223> OTHER INFORMATION: HCDR3 of RM8G-1

<400> SEQUENCE: 8

Val Lys Thr Gly Gln Asp Tyr Ala Val Asp Tyr
1               5                   10

<210> SEQ ID NO 9
<211> LENGTH: 10
<212> TYPE: PRT
<213> ORGANISM: Artificial
<220> FEATURE:
<223> OTHER INFORMATION: CD40 epitope

<400> SEQUENCE: 9

Glu Cys Leu Pro Cys Gly Glu Ser Glu Phe
1               5                   10

<210> SEQ ID NO 10
<211> LENGTH: 10
<212> TYPE: PRT
<213> ORGANISM: Artificial
<220> FEATURE:
<223> OTHER INFORMATION: CD40 epitope

<400> SEQUENCE: 10

Glu Pro Gln Glu Ile Asn Phe Pro Asp Asp
1               5                   10
```